United States Patent
Pommi (10) Patent No.: US 7,488,108 B2
(45) Date of Patent: Feb. 10, 2009

(54) METHOD OR "DEVICE" FOR THE DETERMINATION OF A POSITION OF A PATIENT DURING A CREATION OF AN IMAGE OF AN EXAMINATION AREA OF THE PATIENT BASED ON A MEDICAL IMAGING PROCEDURE

(75) Inventor: Doris Pommi, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 207 days.

(21) Appl. No.: 11/499,832

(22) Filed: Aug. 4, 2006

(65) Prior Publication Data

US 2007/0030957 A1 Feb. 8, 2007

(30) Foreign Application Priority Data

Aug. 4, 2005 (DE) ........................ 10 2005 036 852

(51) Int. Cl.
*A61B 6/08* (2006.01)
(52) U.S. Cl. ............................. 378/205; 378/98; 378/62
(58) Field of Classification Search ......... 378/205–206, 378/98, 98.2, 62
See application file for complete search history.

(56) References Cited

U.S. PATENT DOCUMENTS

| | | | |
|---|---|---|---|
| 5,124,524 A | 6/1992 | Schuster et al. | |
| 6,501,818 B1 * | 12/2002 | Ali et al. | 378/4 |
| 7,077,568 B2 * | 7/2006 | Hornegger | 378/206 |
| 2003/0108154 A1 * | 6/2003 | Schmitt | 378/115 |
| 2003/0233540 A1 * | 12/2003 | Hayashida et al. | 378/98.8 |
| 2006/0104412 A1 * | 5/2006 | Kawanabe | 378/20 |

FOREIGN PATENT DOCUMENTS

DE 199 12 708 A1 9/2000

OTHER PUBLICATIONS

"Digital Imaging and Communications in Medicine (DICOM)", Part 3: Information Object Definitions, 2004, pp. 256-261, 268, 272, 357, 472, 345, 562, 574-575, 578, 818, 12-22, National Electrical Manufacturers Association, Rosslyn, Virginia, USA.
Thomas M. Lehmann, O. Güld, Daniel Keysers, Henning Schubert, Michael Kohnen, Berthold Wein, "Determining the View of Chest Radiographs", Journal of Digital Imaging, Sep. 2003, pp. 280-291, vol. 16, No. 3.

* cited by examiner

*Primary Examiner*—Hoon Song (57) ABSTRACT

In general, the invention relates in general to a determination of a position of a patient who is located in a position provided for the creation of an image according to a medical imaging procedure. According to the invention, the position of the patient is determined automatically based on two complementary body directions of the patient that can be entered by the user with respect to a surface image of the examination area of the patient. In particular, a line is positioned with a computer mouse for each body direction in the image for the identification of the two body directions. In the context of this invention, a corresponding method and a corresponding device are claimed.

20 Claims, 6 Drawing Sheets

METHOD OR "DEVICE" FOR THE DETERMINATION OF A POSITION OF A PATIENT DURING A CREATION OF AN IMAGE OF AN EXAMINATION AREA OF THE PATIENT BASED ON A MEDICAL IMAGING PROCEDURE

CROSS REFERENCE TO RELATED APPLICATIONS

This application claims priority of German application No. 10 2005 036 852.2 filed Aug. 4, 2005, which is incorporated by reference herein in its entirety.

FIELD OF THE INVENTION

The invention relates to a method or a "device" for the determination of a position of a patient during a creation of an image of an examination area of the patient based on a medical imaging procedure.

BACKGROUND OF THE INVENTION

When producing an image of a patient with the help of a medical imaging procedure, a respective position of the patient is normally noted. Known imaging procedures are, for example, classical projection radiography, computer tomography, magnetic resonance tomography or imaging based on ultrasound. Depending on the imaging procedure used, the image is available, for example, in the form of a projection image, a cross-section or a 3D image. With a digital image, the respective position of the patient is normally saved with the digital image as additional information. According to the standard for "Digital Imaging and Communications in Medicine", DICOM for short, at least three different specifications are provided for the patient position: the "Patient Orientation" according to tag 0020,0020, the "Patient Position" according to tag 0018,5100 and the "View Position" according to tag 0018,5101.

DICOM is a standard of the "National Electrical Manufacturers Association", NEMA for short, and more information can be obtained at the DICOM internet site http:\\medical.nema.org\.

The "Patient Orientation" defines the position of the patient relative to the focal planes of the respective image and is the result of a concatenation of two parts, whereby the first part specifies the direction of the image lines from left to right, and the second part specifies the direction of the image columns from top to bottom. Six basic directions are provided for the indication of each part: "Head" in the direction of the head of the patient, "Feet" in the direction of the feet, "Anterior" in the direction of the front side of the body, "Posterior" in the direction of the back side of the body, "Right" in the direction of the right side of the body and "Left" in the direction of the left side of the body. The corresponding body directions for body parts are derived from the definitions provided above, whereby a patient standing upright forms the basis, whose arms are located on the respective side of the body, and whose hands opened flat point forward with their inner surfaces. The respective basic directions are normally abbreviated with their respective first letters. If the image lines or the image columns are not aligned primarily with a basic direction, then the respective part of the "Patient Orientation" contains direction information in the form of a concatenation of at least two of the basic directions in which the image lines or image columns point.

The "Patient Position" defines the position of the patient relative to the imaging device with which the respective image is created, and is the result of a concatenation of two parts. "Head First" (HF) is entered in the first part if the head of the patient points to the front side of the imaging device, and "Feet First" (FF) if the feet of the patient point to the front side of the imaging device. One of the following specifications is entered in the second part of the "Patient Position": "Supine" (S) if the face of the patient points upwards, "Prone" (P) if the face of the patient points downwards, "Decubitus Left" (DL) if the left side of the patient points downwards, and "Decubitus Right" (DR) if the right side of the patient points downwards.

For a radiographic imaging procedure, the "View Position" defines the position of the patient with respect to the radiographic line of sight, i.e. the direction from which the X-ray radiation traverses through the body of the patient. The "View Position" consists of only one single part, in which the following information can be entered: "Anterior/Posterior" (AP) if the X-ray radiation traverses through the front side of the body towards the back of the body of the patient, "Posterior/Anterior" (PA) if the X-ray radiation traverses through the back side of the body towards the front of the body of the patient, "Left Lateral" (LL) if the X-ray radiation traverses through the right side of the body towards the left of the body of the patient, "Right Lateral" (RL) if the X-ray radiation traverses through the left side of the body towards the right of the body of the patient. For mixed information for the four entries specified above, the additional four entries "Right Lateral Decubitus" (RLD), "Left Lateral Decubitus" (LLD), "Right Lateral Oblique" (RLO) and "Left Lateral Oblique" (LLO) are provided.

Additional notes on the definition described above for the position of the patient according to the DICOM standard can be gathered from the documentation previously mentioned for this standard. In addition to the definition of the position of the patient according to the DICOM standard, additional definitions are generally known, which are at least partially comparable to the DICOM standard.

For currently common imaging devices, their respective operator must know the respective position of the patient and make note of the respective image of the patient. For an imaging device for the creation of digital images, it is often provided that the respective position of the patient is to be entered by means of an operating console of the imaging device or a computer associated with the respective imaging device. The identification of the respective position of the patient as well as the subsequent entry of the patient position are time-consuming for the operator and can lead to erroneous entries. On the one hand, this leads to the obstruction of the workflow when creating images, and on the other hand, this leads to a possible erroneous diagnosis as a result of an erroneously noted position of the patient. The respective image of the patient is not always identifiable on the basis of the respective image, so, for example, the risk exists that the position of a patient whose heart is located in the right side of the chest is erroneously identified on the basis of a frontal X-ray image of the chest.

From DE 19912708A1 a method and a device for the control of the positioning of an object to be irradiated in the radiation field of an irradiation device is known, whereby at least one partial cross-section or one partial volume data set for the total irradiated volume is included; the actual position of the object relative to the radiation field is determined based on the cross-section recorded. In fact, this allows a type of direct online position control for the correction of a possible erroneous positioning, but does not solve the problem that an identification of the position of the patient based on an X-ray image that is created with X-ray radiation penetrating the body of the patient is prone to errors.

SUMMARY OF THE INVENTION

The object underlying the invention is a rapid and error-free determination of a position of a patient during a creation of an image of an examination area of the patient based a medical imaging procedure.

The solution for this object succeeds by a method and a device according to the independent claims; advantageous embodiments are the subject matter of the subclaims in each case.

Compared to the prior art, the position of the patient is determined in a manner that reduces errors by means of the automatic determination of the position of the positioned patient based on two complementary body directions of the patient, which are entered by the user in a simple manner with reference to a surface image of the examination area of the patient. With the direct reference to the indicated image, the user of the respective imaging device—compared to a determination of the position of the patient entirely by the user—can enter a mere two easily identifiable body directions, which is substantially easier. The two body directions in the surface image of the examination area of the patient are more easily identifiable in an intuitive manner than in the respective image of the examination area, which is created with the imaging device.

The entry of the body directions can be carried out analogously to the information for "Patient Orientation", for example, with the abbreviations H, F, R, L, A, P based on the basic directions specified above. In terms of the two body directions, the word "complementary" is to signify that non-redundant body directions such as, for example, R and L, are entered based on the "Patient Orientation" from the DICOM standards. An example of two complementary body directions would be the basic directions H and R, for example.

The "surface" image, which is created with the help of visible light, for example, is distinguished from a penetrating image such as, for example, an X-ray image created with the help of X-ray radiation penetrating the body, or another image that is created with a medical imaging procedure. In terms of the invention, it is sufficient if the position of the patient is defined entirely by means of the two body directions previously entered in the step for the automatic determination; these two body directions could indicate the position of the patient, for example, by means of an arrow for each that could be superimposed on the respective image.

The comments and information about advantages mentioned above for the method according to the invention also apply in an analogous manner for the device according to the invention. Corresponding embodiments of the method according to the invention and the device according to the invention are described below for the most part either in a formulation of a method or a formulation of a device, provided that the respective other formulation does not deviate appreciably in content.

An imaging device that already exists can be upgraded with the device according to the invention in a simple manner. It is likewise possible for the device according to the invention to already be integrated during the manufacture of the imaging device.

It is advantageous for the invention to be usable in a medical imaging procedure in the form of a tomography procedure, for which the position of the patient can often be assessed only with difficulty. For a tomography procedure, a cross-section or a 3D image of the patient is created, whereby a C-arm X-ray device, an X-ray computer tomograph or a magnetic resonance tomograph is used as an imaging device. Through a creation of the surface image from an imaging direction that shows a definable relative direction to the respective imaging device, a particularly simple automatic determination of the position of the patient is possible. In particular, in this case a known direction for the imaging direction relative to the imaging device enables the particularly easy determination of the position of the patient relative to the imaging device.

The invention can also be used advantageously in a medical imaging procedure in the form of a two-dimensional imaging procedure with a definable line of sight to the patient; such an imaging procedure is projection radiography, for example, in which the respective line of sight is identified by the respective position of the X-ray device used to create the X-ray image, or the X-ray recipient. The variety of possible positions of the patient is particularly high in the two-dimensional imaging procedure, such that an automatic determination of the position based entirely on two body directions entered by the user represents a particularly great simplification of work. This embodiment also enables the position of the patient to be correlated with the respective line of sight, for example. By creating the image from an imaging direction that basically corresponds to the respective line of sight, the determination of the position of the patient is particularly easy; through this close correlation of the two mentioned directions, it is possible to determine in a particularly easy manner the position of the patient relative to the focal plane for the respectively created image on the basis of the body directions entered in relation to the surface image. However, it is also conceivable for the surface image to be created from a line of sight opposite to the imaging direction. The application to a two-dimensional imaging procedure in the form of a projection process based on X-ray radiation is provided for this purpose.

According to an embodiment of the invention, it is provided that information going beyond the actual examination area to its surroundings in the image is to be represented, and the identification of the respective body directions are thereby simplified for the user, as the case may be. This is the case, for example, if the examination area corresponds to a small section of the back that has structures that are only barely recognizable. If an arm or a leg of the patient is also imaged in the image in addition to this section of the back, then the respective body direction relative to the area of the back is clearly recognizable on the basis of the position of the arm or the leg. For an imaging procedure based on X-ray radiation, it is also possible to limit the integration area to the respective desired examination area in a simple manner based on the displayed image by means of a display of the respective overlay area of the X-ray radiation in the image extended to the surroundings of the examination area.

According to an embodiment of the device according to the invention, its imaging device for creating the digital surface image of the examination area is designed in the form of a digital camera; digital cameras suitable for this applicable can be obtained inexpensively and can be integrated into the device easily. The digital camera can also be provided for the creation of a surface thermal image based on infrared light.

According to an embodiment of the invention, one design of the imaging device for the device is provided in the form of a familiar laser scanner, in particular in the form of a 3D laser scanner; by doing so, a particularly accurate image of the respective examination area of the patient is made possible even without an additional source of light. Any projection of light that might disturb or unsettle the patient is foregone with a laser scanner that works in the range of infrared light.

The image is displayed on a display device of an operator console provided for controlling the creation of the image in a manner that is constructively easy and particularly user-friendly for the user. The shared use of a display device that is already available spares the need for an additional display device. In addition, the user needs to give his attention to only one display device when creating the image or when entering the two body directions.

There are several options for the entry by the user of the two complementary body directions of the patient with respect to the image. According to an embodiment of the invention, the two body directions are entered in each case through a positioning of a line perpendicular to the respective body direction on the one hand, and in a position shifted in the respective body direction with respect to the image compared to the examination area on the other hand; this graphical entry makes a particularly easy identification of the respective body direction possible through the orientation of the respective line in the image, which means parallel to a body contour of the patient. The position shifted in the respective body direction compared to the examination area serves for distinguishing, for example, the basic directions Left and Right or Head and Feet.

According to an additional embodiment of the invention, the two body directions are entered in each case through the positioning of an arrow pointing in the respective body direction with respect to the image; the respective body direction can be identified through the respective arrow in an intuitive manner in particular, immediately and therefore easily.

For the particularly easy entry of the two complementary body directions, in particular through the entry of the lines and arrows specified above, a graphical input device, such as a computer mouse for example, is provided; with this graphical input device, the body directions can be identified in an intuitive manner in the image.

The position of the patients can be set in relation to various ways. According to an embodiment of the invention, the position of the patient is determined relative to the focal plane; this makes it possible to take the position of the patient into account in a simple manner in a diagnosis based on the respective image. The position of the patient relative to the focal plane can be determined with particular ease in the data format for the mentioned DICOM tag 0020,0020 "Patient Orientation", and it can also be saved in this data format, as the case may be. The determination of the position of the patient relative to the focal plane based on an image with an imaging direction that basically corresponds to the respective imaging direction for the creation of the image succeeds with particularly limited effort.

According to a further advantageous embodiment of the invention, the position of the patient is determined relative to the imaging device with which the image is created. The position of the patient relative to the focal plane can be determined with particular ease in the data format for the mentioned DICOM tag 0018,5100 "Patient Position", and it can also be saved in this data format, as the case may be. The determination of the position of the patient relative to the imaging device succeeds with particularly limited effort by taking into consideration the respective orientation of the imaging direction relative to the imaging device with which the image is created.

According to a further advantageous embodiment of the invention, the position of the patient is determined relative to the respective line of sight from which the image is created with the imaging device. For a radiographic imaging procedure, the position of the patient relative to the respective line of sight can be determined with particular ease in the data format for the mentioned DICOM tag 0018,5101 "View Position", and it can also be saved in this data format, as the case may be. The determination of the position of the patient relative to the line of sight succeeds with particular ease by taking into consideration the respective orientation of the imaging direction relative to the line of sight.

Based on the two body directions entered by the user with respect to the image, the position of the patient is determined advantageously in a data format that conforms to the DICOM standard.

By saving the respective position of the patient together with the respective created image, in particular in a data format in conformance with the DICOM standard, the position of the patient is accessible with little effort in connection with the image; for example, the respective position of the patient can therefore be taken into consideration during the diagnosis based on the image. The storage of the aforementioned data can take place in a database in the form of a PACS system, for example.

An exemplary embodiment of the method according to the invention for the determination of a position of a patient—in this embodiment—relative to the focal plane of a digital, two-dimensional X-ray image of an examination area of the patient created with the help of X-ray radiation radiated towards a patient in a radiation direction, includes the following steps:

Positioning the patient in the position provided for the creation of the X-ray image, Creation of a digital surface image of the examination area from an imaging direction basically parallel to the radiation direction, Display of the image, Entry by the user of two complementary body directions of the patient with respect to the image, Automatic determination of the position of the patient relative to the focal plane based on the two body directions.

BRIEF DESCRIPTION OF THE DRAWINGS

The invention as well as additional advantageous embodiments of the invention according to features from the subclaims are described in greater detail below in the drawing on the basis of schematically represented exemplary embodiments, without a limitation of the invention to these exemplary embodiments taking place as a result; they show:

DETAILED DESCRIPTION OF THE INVENTION

Figure 1:
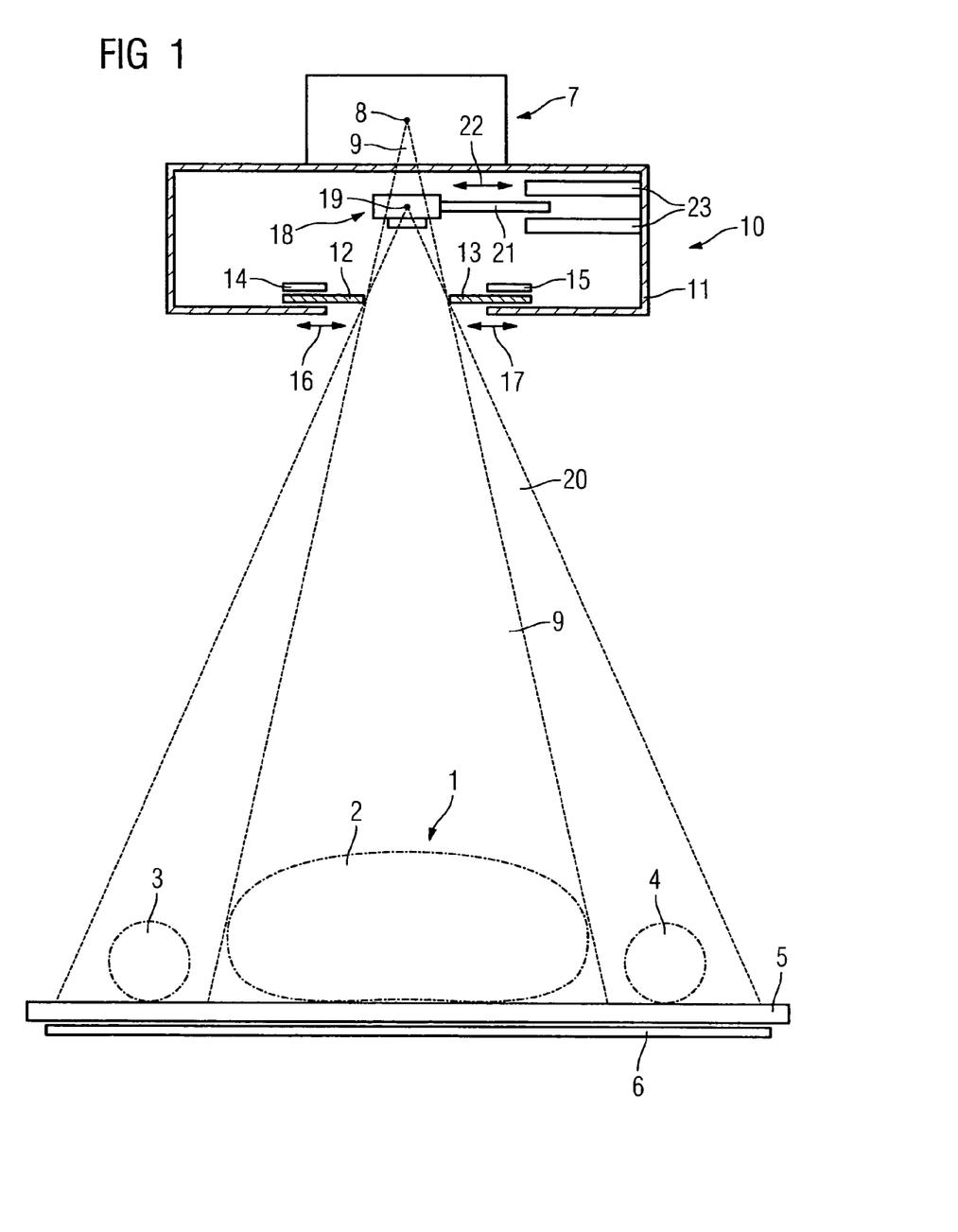
FIG. 1 in a lateral cross-section, an X-ray device for the creation of an X-ray image of a patient with the help of X-ray radiation with a movable digital camera for the creation of a surface image of the examination area in the area of the X-ray radiation.

FIG. 1 shows an X-ray device for the creation of a digital two-dimensional X-ray image of an examination area of a patient 1 lying on a patient bed 5. For the creation of the X-ray image, the examination area can be irradiated with X-ray radiation 9 with an X-ray device 7, which passes through both the patient 1 as well as the patient bed, and which appears on an X-ray detector 6 that creates the respective X-ray image. The X-ray radiation 9 comes out of an X-ray radiation focus 8 in the X-ray device 7, and is isolated by diaphragm blades 12, 13 located in an X-ray device front end 10 at a designated area. The diaphragm blades 12 and 13 are located in the housing 11 of the X-ray front end 10 and can be moved in the movement directions 16 and 17 with the help of a mount 14 or 15 in each case. With their mounts 14 and 15, the diaphragm blades 12 and 13 together form the depth diaphragm for the X-ray device. In addition, an imaging device in the form of a digital camera 18 is provided for the creation of a digital surface image of the examination area of the patient 1.

The digital camera 18 is held by a mount 21, 23 and is adjustable into a first mount position between the X-ray device 7 on the one hand and the patient 1 on the other hand; by doing so, the imaging direction for the digital camera 18 is caused to basically correspond to the radiation direction for the X-ray radiation 19, such that the image created with the digital camera 18 makes the position of the patient 1 identifiable in a particularly easy manner with respect to the focal plane of the X-ray image.

The mount for the digital camera 18 consists on the one hand of a mount arm 21 associated with the digital camera, and on the other hand of a mount arm lead 23, whereby the digital camera 18 is movable by moving the mount arm 21 in a movement direction 22 relative to the mount arm lead 23 in the area of the X-ray radiation 9 as well as a second mount position outside of the area of the X-ray radiation 9. In the initial mount position shown, the digital camera 18 is located between the X-ray device 7 on the one hand and the depth diaphragm 12-15 on the other hand, such that the field of view for the digital camera 18 is limited to the patient 1 by the diaphragm blades 12, 13. However, because the focus 19 for the digital camera 18 is located closer to the diaphragm blades 12, 13 than the X-ray radiation focus 8, the field of view 20 for the digital camera 18 has a larger aperture angle than the area of the X-ray radiation 9. As a result, not only is the examination area as defined by the area of the X-ray radiation 9 indicated by the digital camera 18, but the surroundings of this examination area are shown as well. In this exemplary embodiment only the upper body 2 of the patient 1 is irradiated with the X-ray radiation 9, whereas both the right arm 3 of the patient 1 and his left arm 4 are included with the upper body 2 in the field of view 20.

Instead of the arrangement with the digital camera 18 in the housing 11, positioning it outside of the housing 11 is also possible, in particular underneath the housing 11 laterally beside the area of the X-ray radiation 9; with the digital camera 18 in this position, an X-ray device already available can be equipped with particular ease.

Prior to the creation of the X-ray image by the X-ray radiation 9, the image for the examination area in the initial mount position is created with the help of the digital camera 18; then the digital camera 18 is shifted to the second mount position, and the X-ray image is created with the help of the X-ray radiation 9. According to this anticipated approach, at no point in time is the digital camera 18 exposed to the X-ray radiation 9, because it is shifted into the second mount position outside of the area of the X-ray radiation 9 before the X-ray radiation 9 is radiated. It is also possible to create the image only after the creation of the X-ray image.

Figure 2:
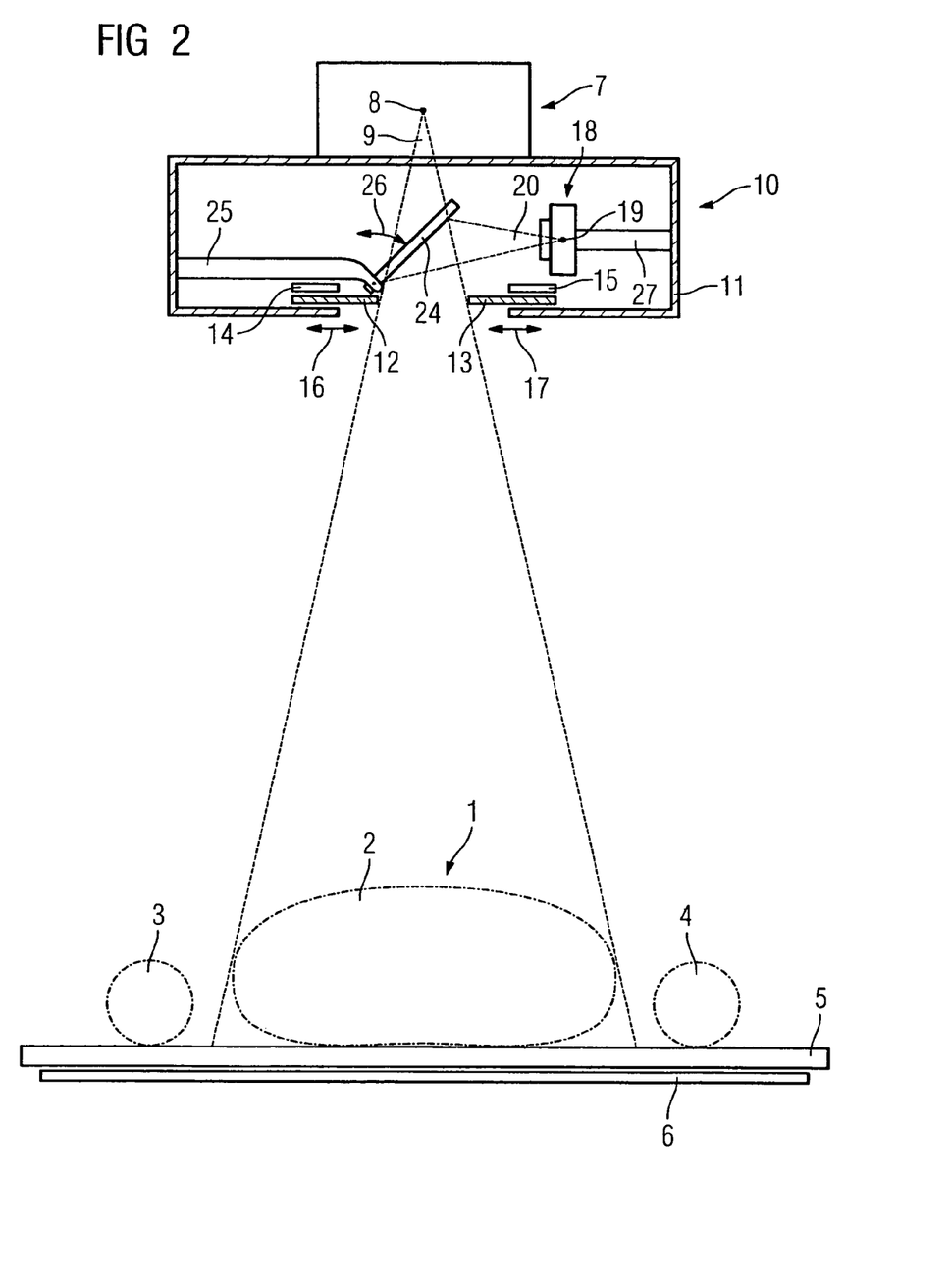
FIG. 2 an X-ray device according to FIG. 1 with a stationary digital camera for the creation of an image using a hinged mirror in the area of the X-ray radiation.

In a lateral cross-section, FIG. 2 shows an X-ray device according to FIG. 1 with a mount 25 for a mirror 24 for its positioning in the first mount position between the X-ray device 7 on the one hand and the patient 1 on the other hand, and with an additional mount 27 for the digital camera 18 for positioning the digital camera 18 outside of the X-ray radiation 9 in such a manner that the examination area can be imaged by the digital camera 18 via the mirror 24; in a constructively simple manner, this mirror 24 allows the creation of the image of the examination area with the help of the digital camera 18 with a line of sight that corresponds to the direction of radiation for the X-ray radiation 9.

The mount 25 for the mirror 24 is designed in such a manner that the mirror can be pivoted in the direction 26 from the first mount position in the X-ray radiation 9 into a second mount position outside of the X-ray radiation 9, such that the mirror 24 can be removed from the area of the X-ray radiation before the X-ray radiation 9 radiates. In the first mount position, the mirror 24 forms an angle with the X-ray radiation 9 of approximately 45° such that the digital camera 18 can be positioned laterally in the housing 11 with space to spare. Because the distance of the X-ray radiation focus 8 from the mirror 24 is identical to the distance of the focus 19 of the digital camera 18 to the mirror 24, the field of view 20 of the digital camera 18 is restricted by the diaphragm blades, 12, 13 in the same manner as the X-ray radiation 9 such that the area of the X-ray radiation 9 beneath the X-ray device front end 10 corresponds with the field of view 20; as a result, the surface image of the examination area created with the digital camera 18 accurately shows the overlay area overlaid in each case by the depth diaphragm 12 through 15, such that not only can the position of the patient 1 be determined in a simple manner on the basis of the image, but the respective overlay area used can be determined as well.

Figure 3:
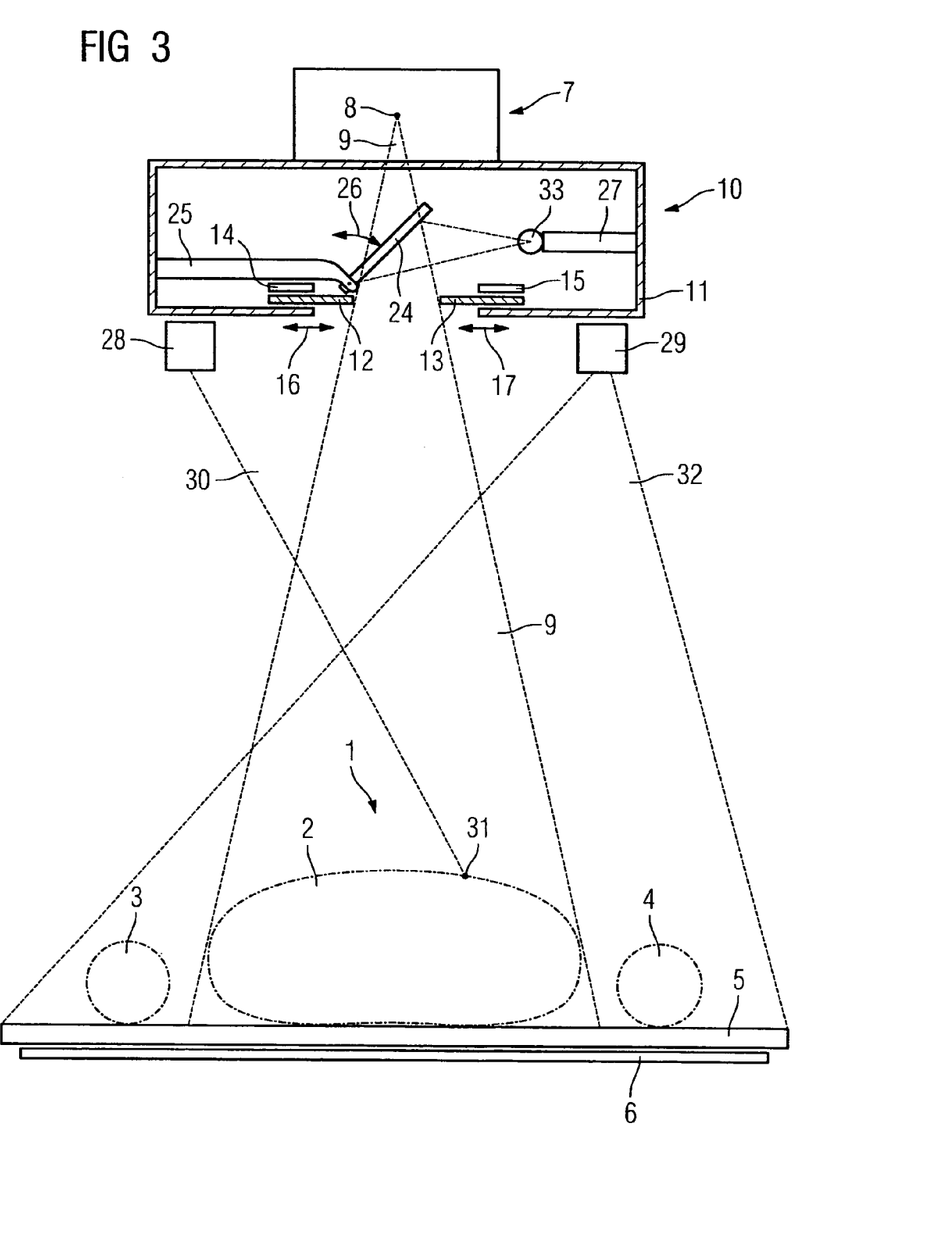
FIG. 3 an X-ray device according to FIG. 2 with a laser scanner for the creation of the surface image of the examination area of the patient instead of the digital camera.

FIG. 3 shows an X-ray device according to FIG. 2 with a laser scanner located underneath the housing 11, which includes a laser emitter 28 located on the left side of the housing 11 on the one hand, and a laser camera 29 located on the right side of the housing 11; this exemplary embodiment involves a laser scanner 28, 29 in the form of a 3-D laser scanner already known from U.S. Pat. No. 5,124,524 for the additional recognition of a depth of the examination area to be penetrated in each case by the X-ray radiation, which can be taken into consideration with the help of the X-ray radiation 9 during the creation of the X-ray image. An illuminant 33 is located at the position of the digital camera 18 and FIG. 2 such that the X-ray device front end 10 together with the mirror 24 takes on the function of a light sight for the display of the respective overlay area for the X-ray radiation 9. The entire scope of U.S. Pat. No. 5,124,524 is included by reference in this text.

The laser emitter 28 radiates a laser beam 30 to the patient 1 at different angles such that a laser projection 31 is visible on the surface of the patient 1. In its field of view 32, the laser camera 29 records this laser projection 31 such that, giving consideration to the respective radiation angle for the laser beam 30, the three-dimensional position of the laser projection 31 can be determined by means of a triangulation. By determining the position of a number of light projections 31, the image of the examination area of the patient 1 is created in the form of a three-dimensional profile.

By positioning the laser scanner 28, 29 in such a way that the image is created principally from the view of the X-ray device 7, it is possible to determine the respective position of the patient 1 relative to the focal plane of the X-ray image created with the X-ray device 7 on the basis of the image in a simple manner. This arrangement can be achieved not only by fastening the parts 28, 29 of the laser scanner to the housing 11 of the X-ray device front end 10, but also, for example, through a respective arrangement by mounting it to other parts of the X-ray device such as, for example, a stand for the X-ray device 7.

Figure 4:
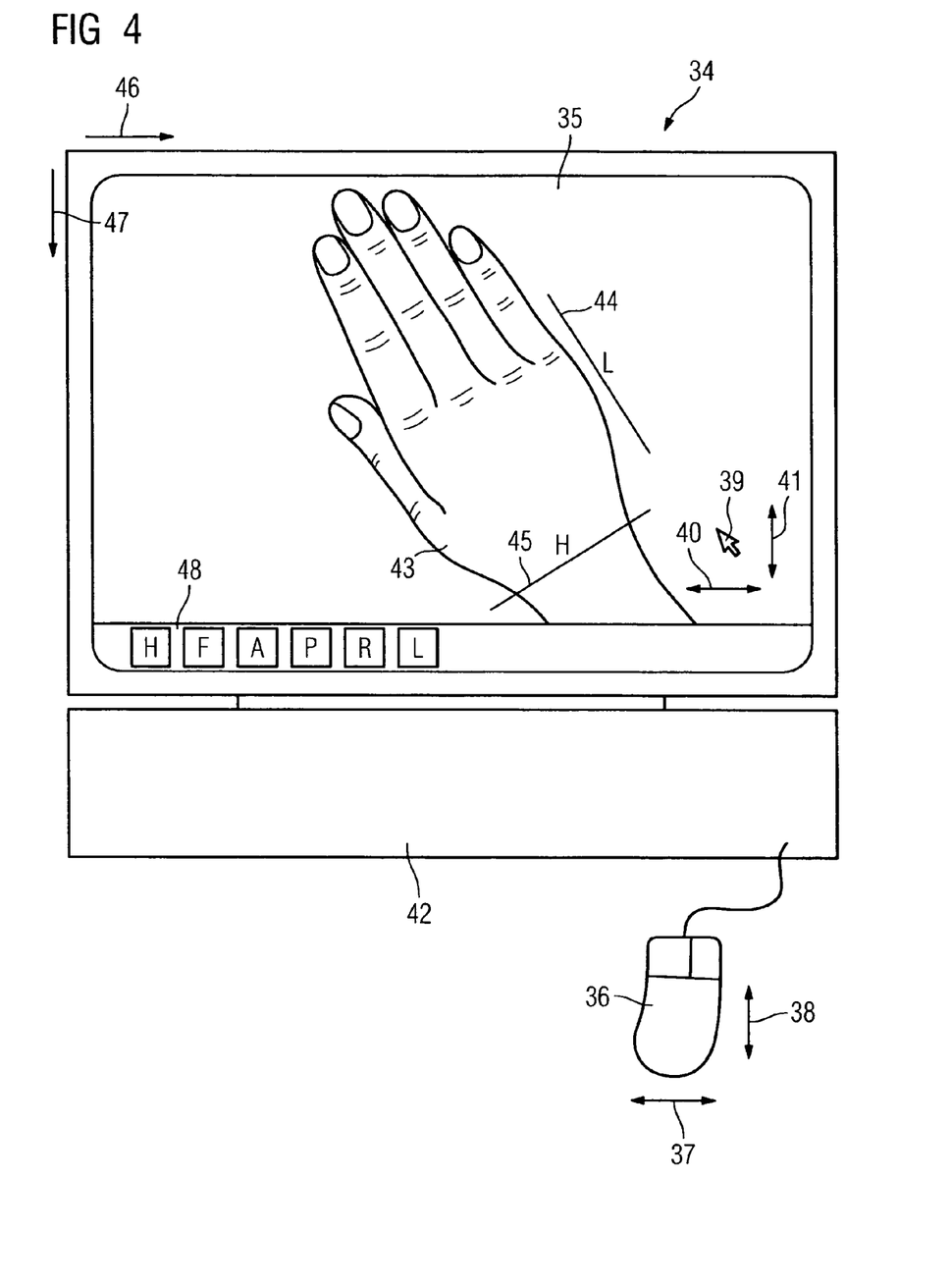
FIG. 4 a screen for the display of the image mentioned above, a computer mouse for the entry of two body directions of the patient by plotting a line in each case on the screen, as well as a computer for automatically determining the position of the patient relative to the focal plane based on the two body directions.

FIG. 4 shows a display device in the form of a computer screen 34, an input device in the form of a computer mouse 36, and a computing device in the form of a computer 42. The computer screen 34 displays an image 35 of a right hand 43 of the patient 1 created with the help of the display resource 18 or 28, 29 mentioned above. With the help of a movement of the computer mouse 36 in a first movement direction 37 or a second movement direction 38, a mouse pointer 39 can be shifted on the computer screen in a first shift direction 40 or in a second shift direction 41.

As shown in FIG. 4, a menu bar 38 can be displayed on the computer screen 34, which shows six symbols that can be selected by clicking with the mouse pointer 39. The symbols are labeled with the abbreviations H, F, A, P, R and L for the six basic directions "Head", "Feet", "Anterior", "Posterior", "Right" and "Left". For the entry of the two complementary body directions of the patient 1 or in this case his right hand 43, at least one of the six basic directions mentioned above is first selected with the mouse pointer 39 in each case, and then a line 44 or 45 is positioned on the image perpendicular to the respective body direction on the one hand and positioned on the image shifted in the respective body direction compared to the hand 43 on the other hand. In this exemplary embodiment, the positioning of the line 44 or 45 is carried out by clicking on the respective starting or ending point of the line 44 or 45 with the help of the mouse pointer 39.

The two body directions "Left" and "Head" are already indicated in this exemplary embodiment through the positioning of the lines 44 and 45 on the computer screen 34. The line 44 for the body direction L is aligned parallel to one side of the hand 43 and located as shifted relative to the hand 43 in the direction of the body direction "Left"; alternatively, a positioning of a line for the basic body direction R parallel to line 44 would be possible on the opposite side of the hand 43. Perpendicular to the line 44 mentioned above for the body direction "Left" is an additional line 45 for the body direction "Head" at the level of the wrist, and thus positioned as shifted in the direction of the body direction "Head" compared to the hand 43. According to the definition of the body directions that are related to a patient 1 standing upright whose arms 3, 4 are located at the respective sides of his body and whose inner hand surfaces point forwards, it is to be noted that the thumbs of the right hand 43 lie in the body direction "Right" relative to the other fingers of the right hand 43, and that the fingers of the right hand 43 point in the body direction "Feet". By selecting more than one basic direction in the menu bar 48, body directions that result from hybrid forms of the basic directions can also be selected.

Based on the two body directions identified with the lines 44 and 45, the computer 42 determines the position of the patient 1 and his hand 43 relative to the focal plane for the respectively created X-ray image. In this exemplary embodiment, the position of the patient 1 is determined in the data format for the DICOM tag 0020,0020 called "Patient Orientation". That body direction that points in image line direction 46 is entered in the first part of this two-part tag, and that body direction that points in image column direction 47 is entered in the second part of this tag. The two parts of the tag each contain one to three abbreviations for the specified basic directions in an ordered sequence, whereby the respective order of the abbreviations specifies with which weight the respective basic direction identifies the respective body direction.

In the present case, the image line direction 46 basically points in the basic direction "Left", which is identified with the line 44 in the image 35, such that the first part of the tag mentioned above starts with the letter L; however, because the hand 43 appears rotated somewhat counterclockwise on the screen 34 compared to a purely vertical direction, the first part of the tag is supplemented with an additional letter H for the basic body direction "Head". The first part of the DICOM tag 0020,0020 therefore reads LH in this case. Because the image column direction 47 basically points in the basic direction "Head" but also somewhat in the basic direction "Right", the second part of the tag mentioned above reads HR. This value for the DICOM tag that is automatically determined by the computer 42 is stored together with the X-ray image of the hand 43 in a PACS system, and can therefore be called up for a later diagnosis. In order to show the respective position of the hand 43 even more precisely, the respective angle of the lines 44 and 45 can also be saved. However, saving the lines 44 and 45 with the X-ray image is also conceivable in order to be able to show the lines 44, 45 in the X-ray image for a later diagnosis.

In addition to the respective position of the patient 1 and the respective X-ray image created, the respective image 35 created can also be saved, in this exemplary embodiment in the form of the PACS system; by doing so, the respective position of the patient 1 determined can be subsequently checked on the basis of the actual position apparent in the image 35. At the same time, the saving of the image 35 takes place independently of a user entry.

In this exemplary embodiment, under additional consideration of a respective position of the X-ray emitter 7, the position of the patient 1 is determined relative to the respective X-ray device or relative to the respective radiation direction; this makes possible an even more detailed determination of position than using a mere determination of the position of the patient 1 relative to the focal plane. The position of the patient 1 can, for example, be determined in the form of the mentioned DICOM tag 0018,5100 "Patient Position", or the mentioned DICOM tag 0018,5101 "View Position". Using the two complementary body directions of patient 1 entered by the user with respect to the image 35, the position of the patient 1 can be determined relative to the respective X-ray device or relative to the respective radiation direction in a simple manner through the computer 42.

To reduce the effort by the user, the entry by the user is made assuming an entry for the body direction determined by an organ program selected in each case. An organ program is a collection of predefined parameters that are used especially for the respective X-ray exposure, among other things the voltage for the creation of the X-ray radiation 9, an exposure time for the creation of the respective X-ray image, special filters, a respective size of the overlay area, a respective anticipated position of the patient 1, and are integrated into the respective organ program according to this embodiment.

Figure 5:
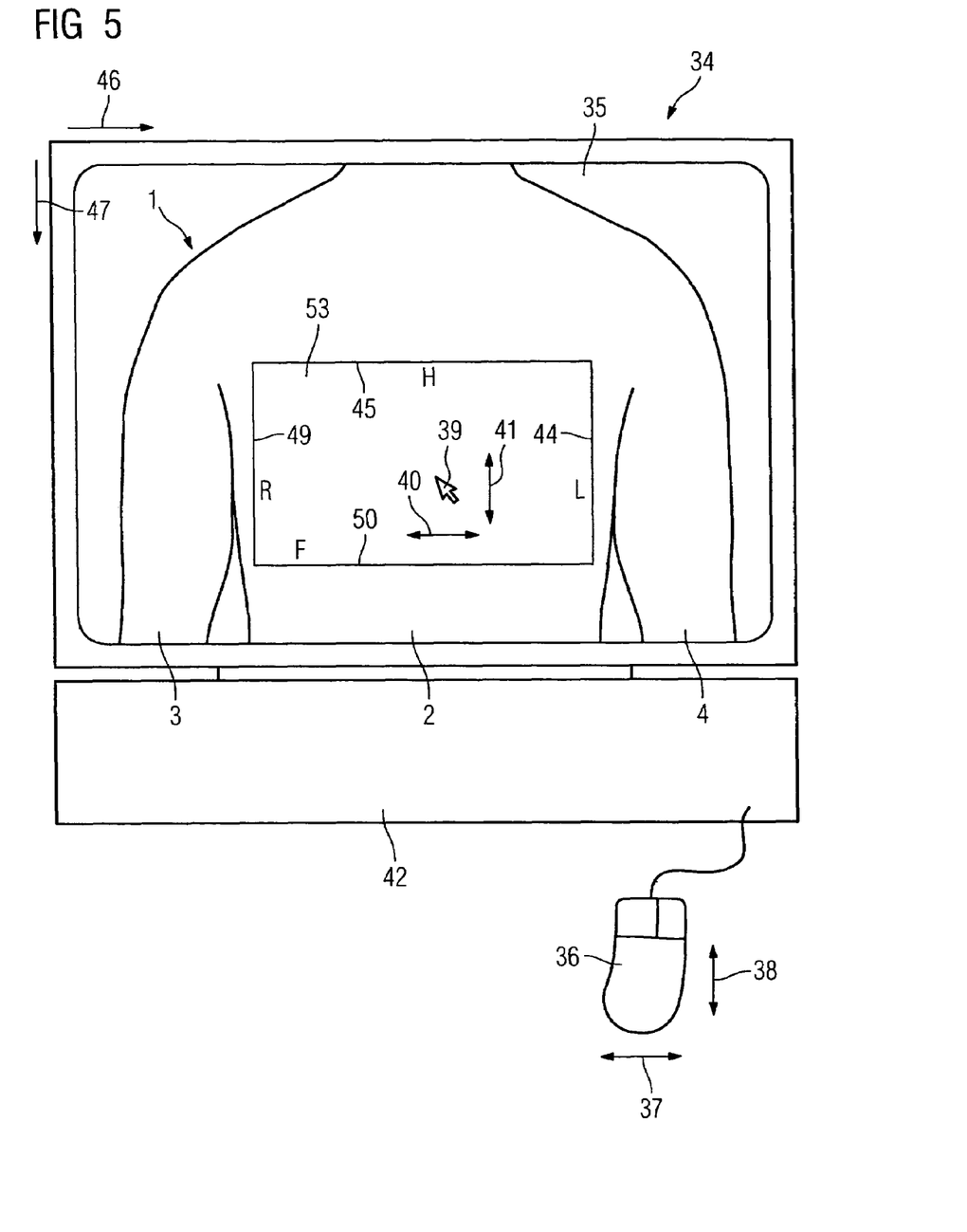
FIG. 5 the objects according to FIG. 4, whereby the overlay area of the X-ray radiation on the examination area is identifiable by plotting the two lines together with the two additional lines.

FIG. 5 shows the same objects 34, 36, 42 as in FIG. 5. In place of the hand 43, the image 35 shows the upper body 2 as well as the right arm 3 and the left arm 4 of the patient 1. As in FIG. 4, a line 44 for the body direction "Left" and a line 45 for the body direction "Right" for identifying the respective body direction are positioned in the image with the help of the computer mouse 36. From the respective position of the lines 44, 45—as in the exemplary embodiment shown in FIG. 4—the position of the patient 1 is determined by the computer 42 in the data format of the mentioned DICOM tag 0020,0020 "Patient Orientation"; the two parts of this DICOM tag read L for Left and F for Feet in this case.

By positioning two additional lines 49 and 50, which are parallel to the initially mentioned lines 44 and 45 in each case, and which together define a rectangle with them, the overlay area 53 provided in each case borders the X-ray radiation 9 at the examination area in a particularly easy manner; an automatic control operated by outside power that relocates the diaphragm blades 12, 13 corresponding to the selected overlay area is provided for this purpose. In this exemplary embodiment the two additional lines 49, 50 are automatically shown in the image 35 after the positioning of two lines 44, 45 that each indicate a body direction, whereby the respective body directions for the two additional lines 49, 50 are specified as based on the two first lines 44, 45 previously entered by the user. With the help of the mouse pointer 39, the respective spacings for the paired parallel lines 44, 49 and 45, 50 can be changed by the user, whereby the length of the four lines 44, 45, 49, 50 can be automatically adjusted in such a way that the four lines 44, 45, 49, 50 together form a closed rectangle that identifies the border of the overlay area 53. The part of the image 53 that lies outside of the overlay area 53 in each case is presented on the screen as darker than the overlay area 53; the overlay area 53 replaces a light projection that can be projected on the surface of the patient 1 with the help of a light sight of the X-ray device for adjusting the depth diaphragm.

Figure 6:
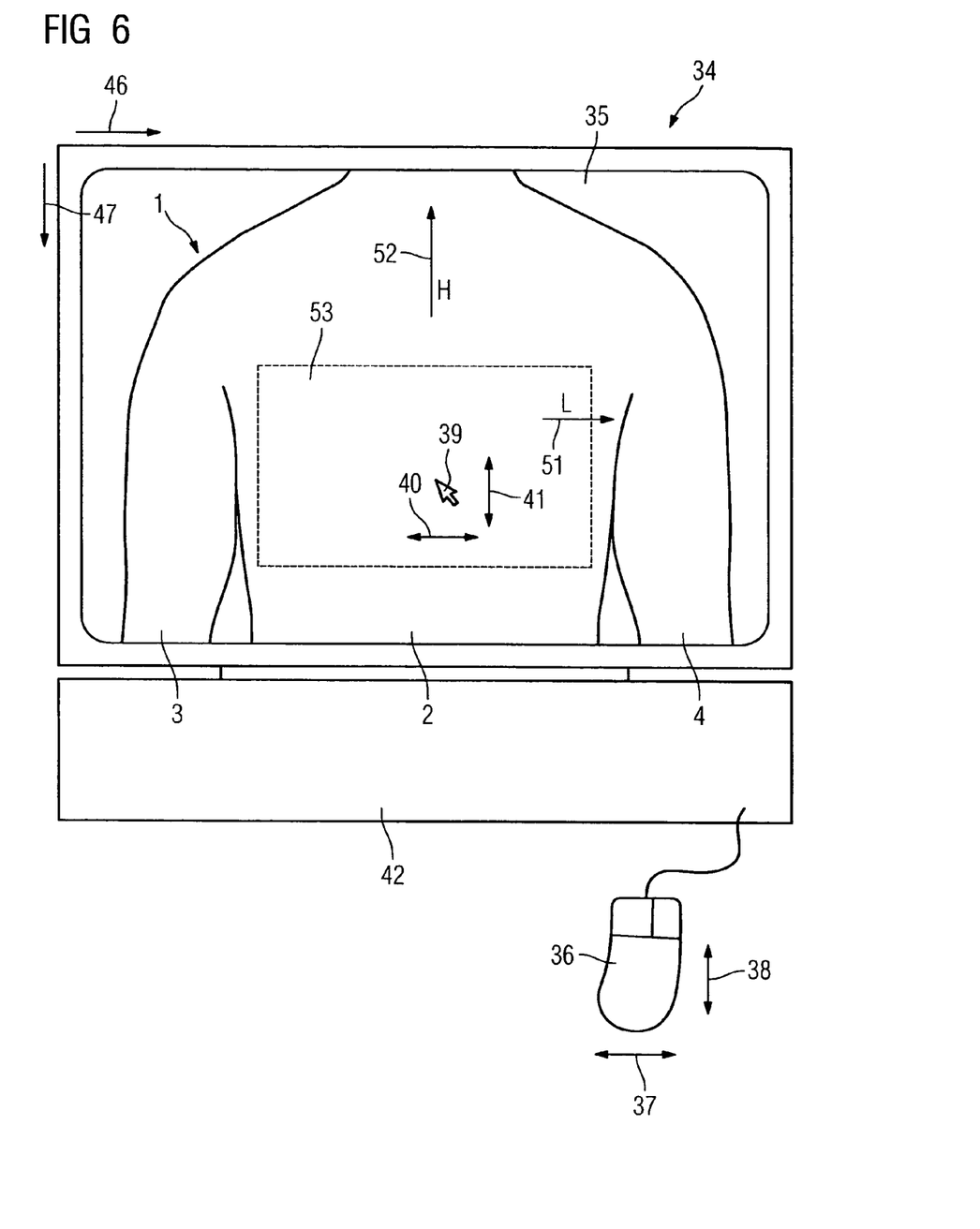
FIG. 6 the objects according to FIG. 5, whereby the two body directions are identifiable in the image by plotting an arrow in each case.

FIG. 6 shows the same objects as FIG. 4 and FIG. 5; as in FIG. 5 the image 35 show the upper body 2 as well as the right arm 3 and the left arm 4 of the patient 2. In this exemplary embodiment, the two complementary body directions are entered in each case by positioning an arrow 51 or 52 pointing in the respective body direction with respect to the image. The respective position of the end of the arrow and the point of the arrow are selected for this purpose in the image 35 with the help of the computer mouse 36. In this case, an arrow 51 points in the body direction "Left" in the image line direction 46, and another arrow 52 points in the body direction "Head" against the image column direction 47. The position of the patient 1 in the data format for the mentioned DICOM tag 0020,0020 "Patient Orientation", which can be determined by the computer based on these body directions entered by the user, therefore reads L for Left in the first part and F for "Feet" in the second part—just like in the exemplary embodiment presented in FIG. 5.

The user's effort for the entry is lessened by an entry of the body directions by the user starting from a prior automatic detection of the body directions. Such a pre-identification is possible with varying identification accuracy, depending on the examination area of the patient 1 to be reviewed. Automatic position identifications for X-ray exposures are known from the field of so-called "Computer Aided Diagnosis" (CAD); such a position identification with respect to the chest area of a patient is known, for example, from the article "Determining the View of Chest Radiographs" by T. M. Lehmann, O. Güld, D. Keysers, H. Schubert, M. Kohnen, B. B. Wein, appearing in "Journal of Digital Imaging", Vol. 16, No. 3, 2003, pages 280-291.

In this exemplary embodiment, the X-ray radiation 9 is displayed in the image 35 in addition to the respective overlay area 43, such that the respective position of the diaphragm blades 12, 13 in the depth diaphragm is adjustable depending on the overlay area 35 displayed in each case.

The procedure described above and the device described above can also be used in each case on an X-ray device that has no patient bed; such an X-ray device is, for example, a raster wall device in which the patient stands in front of the X-ray detector for the creation of the X-ray image.

Instead of placing the imaging device in the vicinity of the X-ray emitter, locating the imaging device in the vicinity of the X-ray detector is also possible; in both cases the image of the patient is created from an imaging direction that is basically parallel to the radiation direction, and thus allows a determination of the position of the patient relative to the focal plane of the X-ray image.

In principle, the invention can be summarized as follows: in general, the invention relates to a determination of a position of a patient who is located in a position provided for the creation of an image according to a medical imaging procedure. According to the invention, the position of the patient is determined automatically based on two complementary body directions of the patient that can be entered by the user with respect to a surface image of the examination area of the patient. In particular, a line is positioned with a computer mouse for each body direction in the image for the identification of the two body directions. In the context of this invention, both a corresponding method as well as a corresponding device are claimed.

The invention claimed is:

1. A method for determining a position of a patient during creation of an image of an examination area of the patient in a medical imaging procedure for said patient, comprising:
   physically positioning the patient in the position for the creation of the image;
   creating a surface image of the examination area of said patient, wherein the surface image of the examination area corresponds to the physical positioning of said patient;
   displaying the surface image;
   entering by an operator two complementary body directions of the patient with respect to the surface image of the examination area of said patient; and
   automatically determining the position of the patient based on the two body directions entered with respect to the created surface image of the examination area of said patient.

2. The method as claimed in claim 1, wherein the image is created by a tomography method in a two-dimensional imaging procedure with a definable line of sight to the patient based on an x-ray radiation.

3. The method as claimed in claim 2, wherein the surface image is created by a digital camera or a laser scanner from a definable direction relative to the imaging device which corresponds to the line of sight and displayed on a display device of an operator console of the imaging device.

4. The method as claimed in claim 1, wherein the two body directions are entered by positioning a line perpendicular to the position for the creation of the image and positioning another line shifted from the examination area parallel to the position.

5. The method as claimed in claim 4, wherein a rectangle which defines an overlay area on the examination area is created by connecting the two lines with two additional lines.

6. The method as claimed in claim 1, wherein the two body directions are determined by a selected organ program or automatically pre-identified.

7. The method as claimed in claim 1, wherein the position of the patient is determined relative to a focal plane of the image or relative to the image device or relative to the line of sight taking into a consideration of an orientation of an imaging direction relative to the imaging device.

8. The method as claimed in claim 1, wherein the position of the patient and the image are saved with a DICOM standard format data.

9. The method as claimed in claim 8, wherein the position of the patient and the image are saved together with the surface image depending on the operator input.

10. A device for determining a position of a patient during a creation of an image of an examination area of the patient in a medical imaging procedure for said patient, comprising:
- an image device for creating the image of the examination area;
- a device for creating a surface image of the examination area of said patient, wherein the created surface image corresponds to a physical position of the patient for the creation of the surface image of the examination area of said patient;
- a display device for displaying the created surface image of the examination area of said patient;
- an input device for inputting two complementary body directions of the patient with respect to the surface image of the examination area of said patient; and
- a computing device for automatically determining the position of the patient based on the two body directions inputted with respect to the created surface image of the examination area of said patient.

11. The device as claimed in claim 10, wherein the image device is an X-ray device and the image is a two-dimensional imaging with a definable line of sight to the patient.

12. The device as claimed in claim 11, wherein the surface image is created by a digital camera or a laser scanner from a definable direction relative to the imaging device which corresponds to the line of sight and displayed on a display device of an operator consol of the imaging device.

13. The device as claimed in claim 12, wherein the digital camera is arranged on a mount at a first position between an X-ray emitter of the X-ray device and the patient in the position for the creation of the X-ray image.

14. The device as claimed in claim 13, wherein a mirror is located in the mount at the first position and the digital camera is arranged on another mount outside of the X-ray radiation such that the surface image is created by the digital camera via the mirror.

15. The device as claimed in claim 13, wherein the first position is between the X-ray emitter and a depth diaphragm of the X-ray device for superimposing the X-ray radiation.

16. The device as claimed in claim 10, wherein the two body directions are input by positioning a line perpendicular to the position for the creation of the image and positioning another line shifted from the examination area parallel to the position.

17. The device as claimed in claim 16, wherein the two body directions are input by positioning an arrow pointing in the position.

18. The device as claimed in claim 10, wherein a rectangle which defines an overlay area on the examination area is created by connecting the two lines with two additional lines.

19. The device as claimed in claim 10, wherein the input device is a graphical input device.

20. The device as claimed in claim 10, wherein the position of the patient is determined relative to a focal plane of the image or relative to the image device or relative to the line of sight taking into a consideration of an orientation of an imaging direction relative to the imaging.

* * * * *